Figure 1:
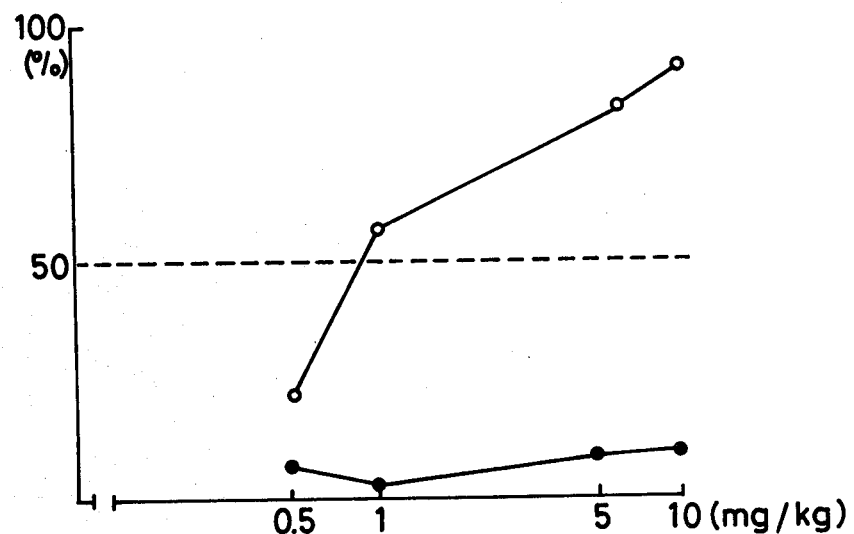

United States Patent [19]

Hiratani et al.

[11] Patent Number: 4,468,344

[45] Date of Patent: Aug. 28, 1984

[54] METHOD OF FRACTIONAL COLLECTION OF GASTRIC ACID SECRETION INHIBITING COMPONENTS

[75] Inventors: Hajime Hiratani, Sennan; Naomi Uchida, Takarazuka; Toyohiko Nishimura, Ashiya, all of Japan

[73] Assignee: Japan Chemical Research Co., Ltd., Hyogo, Japan

[21] Appl. No.: 461,383

[22] Filed: Jan. 27, 1983

[30] Foreign Application Priority Data

Feb. 2, 1982 [JP] Japan ............................... 57-16000

[51] Int. Cl.³ ...................... C07G 7/00; C07G 15/00; C08H 1/00
[52] U.S. Cl. .......................... 260/112 R; 204/180 G; 204/180 R; 424/95; 424/99
[58] Field of Search .............. 260/112 R; 204/180 R, 204/180 G; 424/95, 99

[56] References Cited

U.S. PATENT DOCUMENTS

| | | | |
|---|---|---|---|
| 2,292,841 | 8/1942 | Necheles | 424/99 |
| 2,357,103 | 8/1944 | Gray | 424/99 |
| 3,883,497 | 5/1975 | Gregory | 260/112 R |
| 3,912,704 | 10/1975 | Singh | 260/112 R |
| 4,190,573 | 2/1980 | Zwisler et al. | 260/112 R |
| 4,359,415 | 11/1982 | Sloane | 260/112 R |

OTHER PUBLICATIONS

British J. of Pharmacology, 1971, 41, 8–18, Lawrence et al.

*Primary Examiner*—Howard E. Schain
*Attorney, Agent, or Firm*—Burgess, Ryan & Wayne

[57] ABSTRACT

Gastric acid secretion inhibiting substance obtainable from mammalian urine by conventional method is fractionated into the first and second components by gel filtration, adsorption and desorption on ion exchanger or electrophoresis detecting each component by biological test methods. The activities of the two components differ from each other in the biological tests.

The first component is a glucoprotein-like substance of M.W. 100,000 and the second component is a peptide-like substance of M.W. about 6,000.

6 Claims, 4 Drawing Figures

METHOD OF FRACTIONAL COLLECTION OF GASTRIC ACID SECRETION INHIBITING COMPONENTS

This invention relates to a method of fractionally collecting a gastric acid secretion inhibiting substance present in warm blooded animals.

It is known that a gastric acid secretion inhibiting substance is contained in the body of mammals. Various methods for separating gastric acid secretion inhibiting substance contained in mammalian urine into its components have been suggested, as for instance, acetone powder method by Katzman, et al (J. Biol. Chem. 98, 739 (1932)), ion exchange resin adsorption method by Laurence, et al (Br. J. Pharmacol. 41, 8 (1971)), and activated charcoal adsorption method by R. A. Gregory, et al (J. Physiol. 129, 528 (1955)).

However, the gastric acid secretion inhibiting components obtained by these methods have not been definitely identified, although they believed to be a high molecular glucoprotein.

The present inventors have discovered the presence of two gastric acid secretion inhibiting components in urine which act differently from each other in the body, and have also discovered the presence of there components in the gastric acid secretion inhibiting substance obtained by conventional methods.

For the determination of activity of gastric secretion inhibiting components, the pyloric ligation method in rats by Shay (H. Shay, S. A. Komarov, et al.; Gastroenterogy 5, 43 (1945) may be used. The determination of the acidity of gastric juice accumulated in the stomach of a rat after ligating the gastro-pylorus of a rat, hereinafter called "Shay method".) and perfusion method in rats by Lai (K. S. Lai; Gut. 5, 327 (1964): Determination of the acidity of perfusate over time by previously accelerating the gastric acid secretion with histamine and then infusing a drug (inhibitor) intravenously, hereinafter called "Lai method".) are well known.

The gastric acid secretion inhibiting substance obtained by conventional methods significantly inhibit gastric acid secretion under either one of the afore-mentioned biological test methods. However, this substance can be fractionated in accordance with the research work of the present inventors, into a first component—wherein inhibiting activity is observed by the Shay method but a significant inhibiting activity is not observed by the Lai method—and the second component—wherein inhibiting activity is observed by the Lai method but significant inhibiting activity is not observed by the Shay method.

The first component has a molecular weight of 100,000 and an isoelectric point of 5.6. It is positive ninhydrin and phenol-sulfuric acid tests (M. Dubois et al.; Anal. Chem. 28, 350 (1956)) showing glucoprotein-like properties. For biological testing, this component is active by the Shay method and inactive by the Lai method.

The second component has a molecular weight of approximately 6,000 and an isoelectric point of about 4.6. It is positive to the nihydrin test and negative to the phenol-sulfuric acid test and exhibits peptide-like properties. This second component is active by the Lai method and inactive by the Shay method.

This invention is based on these new findings and is directed to a method of fractionally collecting of gastric acid inhibiting components which comprises fractionating a material containing gastric secretion inhibiting components obtained from mammalian urine by means of at least one procedure selected from gel filtration, adsorption and desorption on an ion exchanger and electrophoresis, and thereby collecting two fractions respectively wherein one fraction possesses gastric acid secretion inhibiting activity by Shay's pyloric ligation method with rats but not by Lai's perfusion method with rats. The other fraction shows gastric acid secretion inhibiting activity by Lai's method but not by Shay's method.

As a material containing gastric acid secretion inhibiting components employed for this invention, gastric acid secretion inhibiting substance obtained from mammalian urine by a known method can be employed. However, it is preferred to check the activity by a biological test beforehand.

The first and second components in the material are fractionated by means of at least one of the following procedures: gel filtration, adsorption and desorption on ion exchanger, and electrophoresis. In these fractionating procedures use is made of the differences in physicochemical properties such as molecular weight, isoelectric points, and affinity to ion exchanger of respective components.

In gel filtration, the two components are fractionated by molecular sieve making use of a difference between molecular weights of the components. Molecular sieve such as Biogel P-10, P-15 and P-20 produced by Bio-Rad Laboratories (Richmond, Calif., U.S.A.), Sephadex G-50, G-75, G-100, Sepharose 6B and Sephacryl S-200 produced by Pharmacia Fine Chemicals AB (Uppsala, Sweden) can be employed. Preference is made for Biogel P-15 and Sephadex G-100.

Fractionation by ion exchanger is based on a difference between isoelectric points and affinity to ion exchanger of the two components. As ion exchanger, cellulose-, polysaccaride-, and polyacrilamide-base ion exchangers are preferably employed. Cellulose-base exchangers are, for example, Whatman CM-cellulose and DEAE-cellulose produced by W. R. Balston Ltd. (Kent, U.K.); polysaccharide-base exchangers are, for example, DEAE-Sephadex, CM-Sephadex and SP-Sephadex produced by Pharmacia; polyacrylamide-base exchangers are, for example, CM-Biogel and DEAE-Biogel produced by Bio-Rad. In addition, any ion exchanger used for separating proteins or peptides, such as styrene-base ion exchange resin may be employed. Dia Ion produced by Mitsubishi Chem. Ind. Ltd. (Tokyo, Japan) and Amberlite produced by Japan Organo Co. Ltd. (Tokyo, Japan) are examples thereof.

Especially preferred ion exchangers are anion-exchangers which are weak in non-specific adsorbability to protein. DEAE-cellulose, DEAE-Sephadex, Amberlite IRA-93 and IR-45 are examples thereof.

Electrophoresis is conducted by preferably utilizing the difference between the two components in isoelectric points. The fractionation is carried out under a conventional method.

The afore-mentioned fractionation procedures can be applied to the two components either individually or in a suitable combination.

Figure 2:
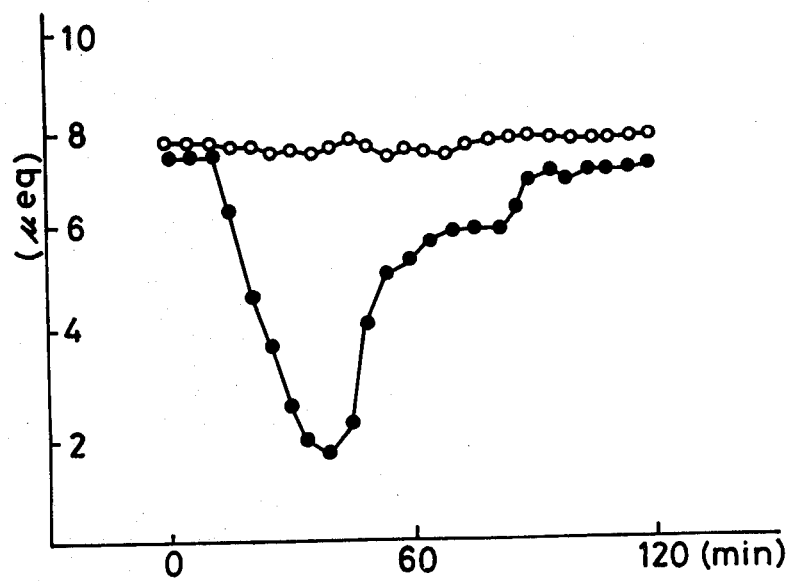
Figure 3:
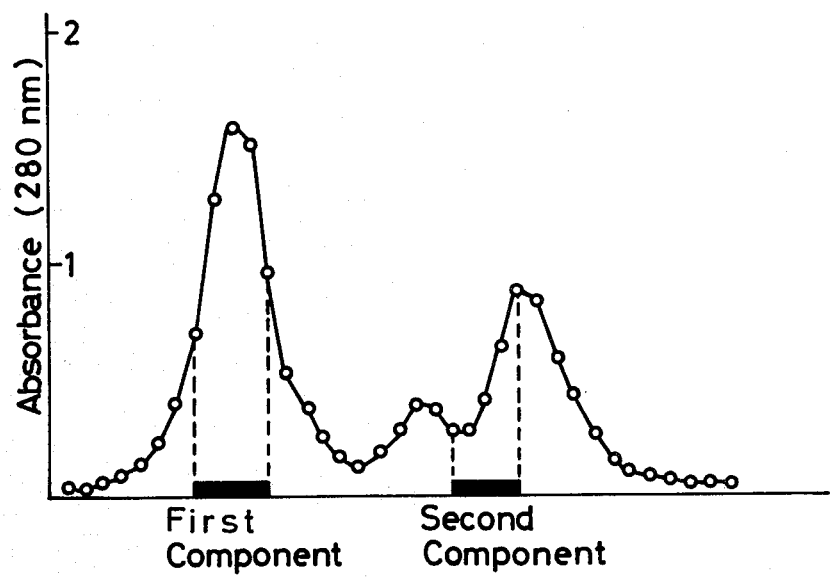
Figure 4:
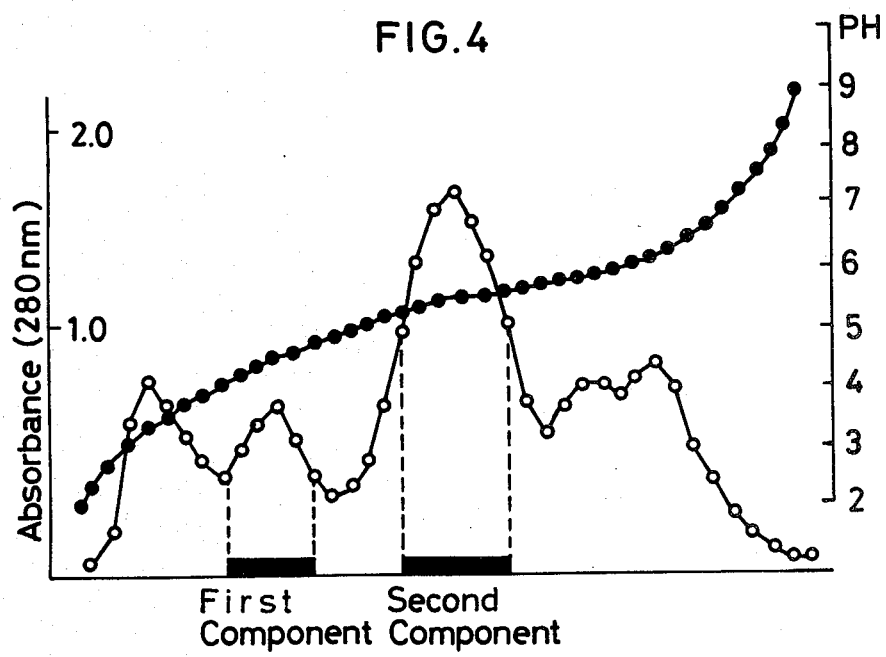

In the drawings, FIGS. 1 and 2 illustrate the test results of Example 1 under Shay and Lai methods. White dots represent the first component, and black dots represent the second component. In FIG. 1 the vertical axis indicates the inhibition rate (%) of gastric acid secretion, and the horizontal axis indicates the dosage (mg/kg) of the respective components. In FIG. 2 the vertical axis indicates the amount of gastric acid secretion (u eq), and the horizontal axis indicates the time (minutes). FIG. 3 illustrates Example 1 wherein fractions of the first and second components were obtained by gel filtration using Sephadex G-100. White dots represent individual fractions, vertical axis indicates absorbance (280 nm) and horizontal axis indicates fraction number. FIG. 4 illustrates Example 6 wherein fractionation of the first and second components was carried out by electrophoresis. Black dots represent absorbance of individual fractions. Vertical axis on the left side indicates absorbance (280 nm), vertical axis on the right side indicates pH and horizontal axis indicates fraction number.

The first component is used in treatment of gastric and duodental ulcers by mouth or injection. Preferable dosage by mouth is 5–10 mg daily.

The second component is used in treatment of keratitis, keratic erosion and keratic ulcer in a form of eye lotion or ointment, furthermore, it is used in treatment of gastric and duodenal ulcers by musclar or intravenous injection as the first component. The concentration of the component in the lotion or ointment is, preferably, 0.5–5 $\mu$g/ml (or g). The lotion or ointment may be applied to the eye in a conventional manner, for example, the lotion is instilled in a dose of 3–4 drops three times a day. For internal administration (injection), the component is used in a dosage within 5–25 $\mu$g daily.

The following examples are further illustrative of this invention.

REFERENCE EXAMPLE 1

6N-hydrochloric acid was added to 5 liters of human urine, and the pH was adjusted to 5.5. With stirring, 500 ml of acetone saturated with benzoic acid was added gradually. After two hours of stirring, the resulting precipitates were collected by filtration to obtain a benzoic acid cake.

This cake was suspended in 500 ml of acetone, and insoluble mattet was collected by filtration, which was washed with a small amount of acetone, dried in a vacuum desiccator to obtain 50 mg of crude dried powder.

This crude material was active at 3.5 mg/kg intravenous administration by tests under both Lai and Shay methods.

EXAMPLE 1

50 mg of crude material obtained in Reference example 1 was dissolved in 10 ml of 0.15M ammonium acetate solution which was poured onto a Sephadex G-100 column ($\phi$2.8×90 cm). Elution was effected with 0.15M ammonium acetate solution, and the eluate was collected by 5.0 ml each fraction. Absorbance at 280 nm was determined, and the first and second components were confirmed as shown in FIG. 3. The components were lyophilized respectively, thus obtaining 20 mg of the first component and 5 mg of the second component. In accordance with gel filtration, molecular weights of the first and second components were approximately 100,000 and 60,000, respectively. Isoelectric point of the first component was approximately pI 5.6 and that of the second component was approximately pI 4.6.

Furthermore, the results of biological test for intravenous administration of 1 mg/kg of each component indicated that the first component was active by Shay method but inactive by Lai method, and that the second component was inactive by Shay method but active by Lai method.

To explain in detail, Shay method was carried out using a group of ten rats wherein 0.2 ml of solution prepared by dissolving the sample in physiological saline at respective concentrations was administered into the tail vein. After four hours acidity of the deposited gastric acid was measured. Based on the acidity of the control group administered with physiological saline, gastric acid secretion inhibiting rate (%) was calculated. The results are shown in FIG. 1.

Lai method was carried out by administering dropwise histamine at a rate of 10 ug/kg/hour to femoral vein of rats, thereby accelerating gastric acid secretion. Subsequently, 0.2 ml of sample was intravenously administered, and physiological saline at a rate of 10 ml/7 minutes was perfused into the stomach. The acidity of perfusate flowing out of gastric cannula was measured with the passage of time, and thus amount of gastric acid secretion was measured. The results are shown in FIG. 2.

EXAMPLE 2

Example 2 was carried out using the same procedure as Example 1, except for a replacement of Sephadex G-100 with Biogel P-10 and 0.1M ammonium acetate solution instead of 0.15 ammonium acetate solution employed in the process of dissolution of crude material and elution with column. 20 mg of dried first component powder and 5 mg of dried second component powder were obtained.

EXAMPLE 3

Example 3 was carried out using the same procedure as Example 2, except for a replacement of Biogel P-10 with Sephacryl S-200, whereby the first component and the second component similarly obtained.

REFERENCE EXAMPLE 2

The pH of 5 ml of human urine was adjusted to 5.6 with 6N-hydrochloric acid. After ending 250 ml of 25% (w/v) tannic acid solution, the mixture was allowed to stand at a cool place for 12 hours. The supernatant was mostly removed by decantation, and the precipitates separating out were filtered and washed with methanol. The residue was extracted with 5 ml of 1% HCl-methanol. The extract solution formed was collected by centrifugation, washed with ether, and dried in vacuum desiccator. Thus, 45 mg of crude material was obtained.

Activity was detected from this crude material with 3 mg/kg intravenous administration by both tests under Lai and Shay methods.

EXAMPLE 4

Employing 45 mg of crude material obtained in Reference example 2, the same procedure as Example 2 was carried out, except 0.15M ammonium acetate solution was employed for dissolution of the crude material and elution of the adsorbed material, thereby giving 15 mg of the first component as dry powder and 3 mg of the second component as dry powder.

EXAMPLE 5

45 mg of crude material obtained in Reference example 2 was dissolved in 50 ml of 0.05M ammonium acetate buffer solution (pH 5.2) and was poured onto Amberlite IR-45 column (2×25 cm) equilibrated with the same buffer solution. The first component was not absorbed on the column and flowed through. The solution was then lyophilized, and thus 15 mg of dried first component powder was obtained. On the other hand, the column was subjected to elution with 50 ml of 0.2M ammonium acetate buffer solution (pH 4.5) and the eluate was lyophilized, thus obtaining 2.5 mg of the second component as dry powder. The biological test results of each component were the same as mentioned in Example 1.

EXAMPLE 6

80 mg of crude material obtained in Reference example 1 was placed in a 110 cm preparative column (LKB) with Ampholine sucrose density gradient containing 1% Ampholine (pH range 3.0–10.0) and charged at 900 V for 72 hours. 2 ml of internal solution of the column was eluted fractionally, and 280 nm absorbance and pH of respective fractions were determined, the results being shown in FIG. 4. 12 ml of the fraction containing the first component around pH 5.6 and 10 ml of the fraction containing the second component around pH 4.6 were obtained.

Using a Sephadex G-150 column (2×50 cm) equilibrated with 0.1M ammonium acetate solution, each fraction was desalted and lyophilized. Thus, 24 mg of the first component as dry powder and 12 mg of the second component as dry powder were obtained.

We claim:

1. A method of isolating gastric acid secreting inhibiting substances from body fluids containing the same comprising:
    (a) subjecting said fluid to at least one fractionation method selected from gel filtration, adsorption and desorption using an ion exchanger and electrophoresis to obtain a first substance having a molecular weight of about 100,000 and an isoelectric point of 5.6 and a second substance having a molecular weight of about 6,000 and an isoelectric point of about 4.6;
    (b) determining the presence of said first and second substance by subjecting the same to the Shay pyloric ligation test and the Lai perfusion test, wherein said first component is substantially active by the Shay test and substantially inactive by the Lai test and wherein said second component is substantially active by the Lai test and substantially inactive by the Shay test.

2. A method according to claim 1 wherein the two fractions are fractionated by gel filtration.

3. A method according to claim 1 wherein the two fractions are fractionated by adsorption and desorption on ion exchanger.

4. A method according to claim 1 wherein the two fractions are fractionated by electrophoresis.

5. A method according to claim 1 wherein the component contained in the fraction active in Shay's method and inactive in Lai's method has a molecular weight of 100,000 and an isoelectric point of 5.6, being positive to nihydrin and phenol-sulfuric acid tests.

6. A method according to claim 1 wherein the component contained in the fraction inactive in Shay's method and active in Lai's method has a molecular weight of approximately 6,000 and an isoelectric point of about 4.6, being positive to ninhydrin test and negative to phenol-sulfuric acid test.

* * * * *

UNITED STATES PATENT AND TRADEMARK OFFICE
CERTIFICATE OF CORRECTION

PATENT NO. : 4,468,344
DATED : August 28, 1984
INVENTOR(S) : Hajime Hiratani, et al It is certified that error appears in the above-identified patent and that said Letters Patent is hereby corrected as shown below:

Column 3, line 11: change "Black" to --White-- line 17: change "duodental" to --duodenal-- line 62: change "60,000" to --6,000.

IN THE DRAWING:

In Fig. 4, change "First Component" to --Second Component--;

change "Second Component" to --First Component--

Signed and Sealed this

Sixteenth Day of April 1985

[SEAL]

Attest:

DONALD J. QUIGG

Attesting Officer     Acting Commissioner of Patents and Trademarks